US010786454B2

(12) United States Patent
Kao et al.

(10) Patent No.: US 10,786,454 B2
(45) Date of Patent: Sep. 29, 2020

(54) AEROSOL LIPOSOME OF MARINE EXTRACT AND METHOD OF PRODUCING THE SAME

(71) Applicant: FISHERIES RESEARCH INSTITUTE, COUNCIL OF AGRICULTURE, Keelung (TW)

(72) Inventors: Yi-Feng Kao, Keelung (TW); Yi-Chen Chen, Taipei (TW); Chwen-Herng Wu, Keelung (TW)

(73) Assignee: FISHERIES RESEARCH INSTITUTE, COUNCIL OF AGRICULTURE (TW)

( * ) Notice: Subject to any disclaimer, the term of this patent is extended or adjusted under 35 U.S.C. 154(b) by 732 days.

(21) Appl. No.: 15/298,331

(22) Filed: Oct. 20, 2016

(65) Prior Publication Data

US 2017/0304202 A1    Oct. 26, 2017

(30) Foreign Application Priority Data

Apr. 20, 2016 (TW) .............................. 105112352 A

(51) Int. Cl.
| | | |
|---|---|---|
| *A61K 35/618* | (2015.01) | |
| *A61K 9/127* | (2006.01) | |
| *A61K 35/60* | (2006.01) | |
| *A61K 31/685* | (2006.01) | |
| *A61K 9/00* | (2006.01) | |
| *A61K 9/12* | (2006.01) | |
| *A61K 45/06* | (2006.01) | |

(52) U.S. Cl.
CPC ............ *A61K 9/127* (2013.01); *A61K 9/0073* (2013.01); *A61K 9/12* (2013.01); *A61K 31/685* (2013.01); *A61K 35/60* (2013.01); *A61K 35/618* (2013.01); *A61K 45/06* (2013.01)

(58) Field of Classification Search
CPC .............................. A61K 35/61; A61K 35/618
USPC ..................................... 424/523, 283.1, 94.3
See application file for complete search history.

(56) References Cited

U.S. PATENT DOCUMENTS

| 5,049,388 A | * | 9/1991 | Knight | ................. | A61K 9/0078 264/4 |
| 2009/0269396 A1 | * | 10/2009 | Cipolla | ................. | A61K 9/0073 424/450 |
| 2012/0321698 A1 | * | 12/2012 | Narain | ................. | A61K 9/0078 424/450 |

FOREIGN PATENT DOCUMENTS

WO     WO-2005055978 A3 *   7/2005   ........... A61K 9/0075

OTHER PUBLICATIONS

Moussaoui et al, "Marinosonnes, marine lipid-based liposomes: physical characterization and potential application in cosmetics", International Journal of Pharmaceutics 242 (2002) 361-365 (Year: 2002).*

* cited by examiner

*Primary Examiner* — Michael Barker
*Assistant Examiner* — Deborah A Davis
(74) *Attorney, Agent, or Firm* — Schmeiser, Olsen & Watts, LLP

(57) ABSTRACT

An aerosol liposome of a marine extract and a method of producing the same are introduced. The marine extract is extracted from cell membranes of marine processing streams, including phosphatidylserine (PS), phosphatidylcholine (PC), phosphatidylethanolamine (PE), phosphatidylinositol (PI), and lysophosphatidylcholine (LysoPC), further including at least phosphatidylserine (PS). The aerosol liposome is of a particle diameter of less than 2,000 nm. The surface of the aerosol liposome carries phosphatidylserine (PS) molecules. The aerosol liposome of a marine extract, thus provided, is simple and stable and can be absorbed through the mouth, nose, upper respiratory tract, and epidermis and engulfed by macrophages therein to quickly alleviate or regulate systematic inflammatory responses and prevent inflammation-related diseases.

9 Claims, No Drawings

AEROSOL LIPOSOME OF MARINE EXTRACT AND METHOD OF PRODUCING THE SAME

CROSS-REFERENCE TO RELATED APPLICATION

This non-provisional application claims priority under 35 U.S.C. § 119(a) on Patent Application No(s). 105112352 filed in Taiwan, R.O.C. on Apr. 20, 2016, the entire contents of which are hereby incorporated by reference.

FIELD OF THE INVENTION

The present invention relates to aerosol liposomes of marine extracts and methods of producing the same and, more particularly, to an aerosol liposome of a marine extract and a method of producing the same, and the aerosol liposome alleviates an inflammatory response.

BACKGROUND OF THE INVENTION

The prior art discloses a phospholipid extracted from marine organisms, such as squid, genetically modified plant seeds or microbes. The phospholipid is rich in EPA, DHA, DPA(n-3, n-6), and ARA. The prior art further discloses a method of extracting the phospholipid. The phospholipid is administered to humans and companion animals in the form of aerosol or particulates, so as to treat EPA deficiency and DHA deficiency and serve pharmaceutical and cosmetic purposes. EPA deficiency and DHA deficiency cause inflammations and immune disorders; in this regard, the phospholipid is anti-inflammatory.

Although the prior art discloses that the extracted phospholipid is applied in the form of aerosol, the disclosed effective ingredients are metabolites of EPA, DHA, DPA and ARA contained in phospholipid molecules, and their efficacy is not verified by any experiment. Furthermore, a subject matter disclosed in the prior art, i.e., phospholipid-based EPA, DHA, DPA and ARA, can be incorporated into aerosol sprays for treating chronic inflammatory disease states of the lung, such as COPD, asthma or cystic fibrosis, but the prior art does not disclose how to incorporate semisolid phospholipid extract into aerosol sprays for delivery to the lung, nor does the prior art disclose how the lung tissue takes in and uses the semisolid phospholipid extract. In short, the prior art discloses that phospholipid-based EPA, DHA, DPA and ARA are anti-inflammatory and thus fit for treating chronic inflammatory diseases, but the disclosure is not supported by any experiments.

The prior art pertaining to liposomes is usually applicable to carriers of drugs or nutrients to protect the drugs or nutrients against an unfriendly environment or deliver the drugs to a target tissue. The liposomes each essentially comprise bipolar molecules. When synthesized according to the prior art, the liposomes work by encapsulating a drug or releasing its contents slowly. The prior art discloses that, in the course of their being taken in by the lung, drugs encapsulated by liposomes elude macrophages and experience metabolism slowly, thereby rendering liposome-encapsulated drugs long-acting.

Synthesis of liposomes by phospholipid polymerization requires that appropriate phospholipid compositions be energized appropriately (for example, be shaken by ultrasound or be blended by hand). Liposome particle diameter depends on the type of the aforesaid driving energy. Solvents play a crucial role in building the hydrophilic and hydrophobic interfaces of the liposomes. The phospholipid is monolayer or bilayer. The aforesaid variations in the phospholipid compromise the efficacy of the phospholipid in alleviating an inflammatory response. The prior art discloses an animal experiment which proves that intra-peritoneal injection of phosphatidylserine-containing liposome (PS-liposome), as opposed to phosphatidylcholine-containing liposome (PC-liposome), to mice is effective in alleviating the swellings and inflammations at the mice' claws. Furthermore, the prior art discloses that, in the course of inevitable cellular aging, intracellular PS molecules go extracellular and turn into apoptotic bodies, whereas apoptotic cells secrete nucleic acids or cytokines to not only entice macrophages and thus get engulfed and eliminated by the macrophages, a phenomenon known as efferocytosis, but also trigger an inflammation suppression mechanism—intrinsically and inoffensively. Hence, depending on their phospholipid compositions, liposomes or apoptotic bodies bring about various physiological functions. Nonetheless, residual cells abound in wastes and processing streams produced as a result of the processing of marine organisms, bringing into question two issues, namely the unproven anti-inflammatory benefit achieved by extracting and recombining cell membrane-derived phospholipid-based apoptotic cells, and the unverified role played by aerosol-based liposomes in regulating macrophagic inflammation.

In view of the aforesaid issues, the present invention discloses a method of recombining cell membrane-derived phospholipid and presenting it in the form of aerosol liposomes, wherein the aerosol liposomes are monolayer or multilayer liposomes made from a marine cell membrane extract. Before the recombination of cell membrane-derived phospholipid, phosphatidylserine (PS) molecules reside inside the bilayer phospholipid membrane. According to the present invention, after the recombination of cell membrane-derived phospholipid, the phosphatidylserine (PS) molecules are exposed on the surfaces of the liposomes and aerosol-based, being destined for the human mouth, nose, upper respiratory tract, and epidermis. The aerosol-based liposomes draw macrophages to get distinguished and destroyed by the macrophages. Furthermore, inflammations are not only alleviated or regulated by efferocytosis, but are also alleviated or regulated instantly because the aerosol-based liposomes are brought into contact with the human mouth, nose, upper respiratory tract, and epidermis.

SUMMARY OF THE INVENTION

It is an objective of the present invention to provide an aerosol liposome of a marine extract, wherein the marine extract is extracted from cell membranes of marine processing streams, including phosphatidylserine (PS), phosphatidylcholine (PC), phosphatidylethanolamine (PE), phosphatidylinositol (PI), and lysophosphatidylcholine (LysoPC), and at least includes phosphatidylserine (PS), characterized in that:

the aerosol liposome is of a particle diameter of less than 10,000 nm, and a surface of the aerosol liposome carries phosphatidylserine (PS) molecules.

The aerosol liposomes are in gas phase/aqueous phase/oil phase (G/A/O), gas phase/oil phase (G/O), or gas phase/oil phase/aqueous phase (G/O/A).

The aerosol liposomes each have a particle diameter of 20~10,000 nm, preferably 50~300 nm.

The aerosol liposomes are essentially monolayer particulates.

Regarding the aerosol liposome, the marine extract is from squid's skin, mackerel's head, milkfish visceras, tilapia visceras, red seabream visceras, and bonitos' visceras.

The aqueous phase of the outermost layer of the aerosol liposome further comprises a member selected from the group consisting of nucleic acid matter, cytokine, and valent ion.

Another objective of the present invention is to provide a method of producing an aerosol liposome, for producing the marine extract aerosol liposome, comprising the steps of atomizing the marine extract into the aerosol liposome with an aerosol atomizer, disrupting and restricting the arrangement of cell membrane-derived phospholipid, thereby producing liposomes of a mimic apoptotic cells.

Regarding the method, marine extract-derived solids, a marine extract-containing solvent, and a marine extract suspension are added to an aqueous solution to get diluted and atomized with an aerosol atomizer to synthesize the aerosol liposomes, and a member of the group consisting of nucleic acid matter, cytokine or valent ion is added to the aqueous solution.

The aerosol liposome of a marine extract, thus provided, is simple and stable and can be absorbed through the mouth, nose, upper respiratory tract, and epidermis and engulfed by macrophages therein to quickly alleviate or regulate systematic inflammatory responses and prevent inflammation-related diseases.

DETAILED DESCRIPTION OF THE PREFERRED EMBODIMENTS

Objectives, features, and advantages of the present invention are hereunder illustrated with specific embodiments, depicted by tables, and described below.

Regarding the features of squid's skin liposomes, conventional bilayer phospholipid is the main constituent of the cell membrane and serves as an important boundary which separates the intracellular space from the extracellular space, thereby enabling intracellular physiological functions to work well. In addition to edibles, marine organism processing produces plenty of processing streams, such as the head, skin, and visceras of fish. The materials are usually presented in the form "fish meal" or fish oil and sold as feed. Unfortunately, the processing streams often contain residual cellular tissues. 150~200 thousand tons of squids are caught by Taiwanese fishermen every year, and the squids are processed to produce processing streams which account for 35% by weight of the aforesaid annual catch. Out of the squid-related processing streams, 15% are squid's skin. In a squid's skin, phospholipid accounts for 80~85% of lipid by weight. In this regard, phospholipid extracted from squid's skin is rich in omega-3 polyunsaturated fatty acids like EPA and DHA. According to the present invention, phospholipids are extracted from squid's skin to produce aerosol-based squid's skin liposomes (hereinafter referred to as "aerosol liposomes"), and then the aerosol liposomes mimic apoptotic cells in being engulfed by macrophages to effectuate efferocytosis and thereby alleviate inflammations.

Extraction of Phospholipid

Take marine extracts, such as squid's skin, as an example, squid's skin is supplied by Mei-er Hau Fishing Co., Ltd (Tainan, Taiwan). The squid's skin is obtained by removing the head, fins, and visceras from squid (*Dosidicusgigas*). Then, the squid's skin is frozen quickly and thus lumped. The extraction of phospholipid from the squid's skin entails cutting the squid's skin into slices, 3~5 mm thick each, with a cutter (Mirra 300, Sirman, IT), mixing 50 g of squid's skin slice and 19 times of volume of 95% ethanol with a homogenizer (Polytron PT 3000, Kinematica, CH) for five minutes, sonicating the mixture with an ultrasonic cleaner (D200H, Delta, TW) in a water bath at 70° C. for 60 minutes, filtering the heated shaken mixture with a Buchner funnel (Buchner type Ryrex 26G4, Iwake, JP) by vacuum filtration, concentrating and drying the filtrate in vacuum, thereby producing ethanol extract. Afterward, the ethanol extract is weighed, and then acetone in 10 times the volume of the ethanol extract is introduced thereto washed out neutral lipid twice or thrice. The residual acetone insoluble matter is the conventional phospholipid which is dried at 70° C., in vacuum, for 1~2 hours to remove the residual acetone, to finalize the extraction of squid's skin phospholipid.

HPLC-UV Analysis of Constituents of Phospholipid (Originated from Squid's Skin and Other Animals)

Take 10 mg of samples (such as squid's skin phospholipid) and dissolve them in 1 ml of ethanol. The constituents of squid's skin phospholipid are analyzed by HPLC analysis with an HPLC system (JASCA PU-2089 plus) in conjunction with a 20 µl sample ring and a UV detector (Shimadzu SPD-6A) to analyze 202 nm absorbance wavelength, with a flow rate of 2 mL/min, a pump critical pressure of 70 MPa, mobile phase of acetonitrile:methanol:sulfuric acid=100:3:0.05, with the analysis-level HLPC column Kromasil (4.6× 250 mm) 60-5Si used in the stationary phase, taking 30 minutes to analyze a single sample, so as to collect and integrate peak signals. Constituents of phospholipid extracted from different marine products are shown in Table 1 below.

TABLE 1

Constituents of phospholipid extracted from different marine processing streams

| Type of phospholipid* | squid's skin (%) | mackerel's head (%) | milkfish's viscera (%) | Tilapia's viscera (%) | red seabream's viscera (%) | Bonitos' viscera (%) |
|---|---|---|---|---|---|---|
| Phosphatidylcholine (PC) | 51.8 ± 3.03 | 44.3 ± 4.2 | 32 | 34 | 28 | 34.6 |
| Phosphatidylethanolamine (PE) | 20.6 ± 0.84 | 30.1 ± 2.7 | 14 | 15 | 9.1 | 11.5 |
| Phosphatidylserine (PS) | 8.6 ± 0.14 | 9.6 ± 0.2 | 7.0 | 9.0 | 6.1 | 5.8 |
| Phosphatidylinositol (PI) | 4.6 ± 0.84 | 3.5 ± 1.1 | 11 | 7.4 | — | — |

TABLE 1-continued

Constituents of phospholipid extracted from different marine processing streams

| Type of phospholipid* | squid's skin (%) | mackerel's head (%) | milkfish's viscera (%) | Tilapia's viscera (%) | red seabream's viscera (%) | Bonitos' viscera (%) |
|---|---|---|---|---|---|---|
| Lysophosphatidylcholine (Lyso-PC) | 5.4 ± 2.82 | 0.3 ± 0.3 | 4 | 1.0 | — | — |
| Others | 9.0% ± 1.03 | 11.9 ± 2.1 | 32 | 33.6 | — | — |

*Types of phospholipid in acetone insolubles which originate from different marine products, as analyzed by HPLC-UV technique.

Referring to Table 1, after squid's skin has undergone ethanol extraction and has had its neutral lipid cleaned by acetone, 3~4 grams (3.5±0.3 g) of phospholipid is extracted from every 100 g (in wet weight) of squid's skin on average. Furthermore, squid's skin and mackerel's head have higher polar lipid content than their counterparts, whereas milkfish's and tilapia's visceras have higher neutral lipid content than their counterparts and thus must be treated with acetone more often than their counterparts to extract the neutral lipid. When analyzed with a high-performance liquid chromatography (HPLC) system together with a UV detector, phospholipids extracted from different marine processing streams are found to contain major constituents: phosphatidylcholine (PC), phosphatidylethanolamine (PE), phosphatidylserine (PS), phosphatidylinositol (PI), lysophosphatidylcholine (Lyso-PC), and others. Among the above constituents, phosphatidylserine (PS) is a required one.

Analysis of Particle Diameter of Aerosol Liposomes (Squid's Skin)

According to the prior art, depending on their appearance, liposomes come in three categories: small unilamellar vesicles (SUV), large unilamellar vesicles (LUV), and multilamellar vesicles (MLV). SUV liposomes feature a small capacity and a particle diameter of 30-50 nm. LUV liposomes each have a particle diameter of 100-500 nm and usually function as carriers for delivering cosmetic or drugs. As its name suggests, MLV are large. Each MLV comprises several concentric small liposomes, has a particle diameter of 200-2,000 nm, and is for use in releasing a drug with different levels of contents.

A method of producing liposomes entails dissolving phospholipids in an organic solvent contained in a flask, forming a film on the inner wall of the flask after the solvent has volatilized, introducing an aqueous solution to the flask and shaking the flask by hand, and waiting for a lipid film to spread until the lipid film takes in water and swells to thereby bend and close, thereby forming the liposomes. The aforesaid method, also known as hand-shaking technique, ends up with MLV liposomes which are not uniform in size. As a result, the MLV liposomes produced by the hand-shaking technique have to be further processed with the other techniques, such as ultrasonic oscillation or squeezing, in order to acquire an ideal liposome size.

According to the present invention, 7.5 mg/mL of squid's skin liposomes (SQ-liposomes) suspension is vibrated with a commercially available atomizer to turn into aerosol liposomes. The vent of the aerosol atomizer is connected to a flocculation pipe to recycle the aerosol liposomes in the form of a liquid. The liposome suspension recycled with the flocculation pipe is added to a disposable cuvette and then analyzed with particle-diameter potentiometer Zetasizer Nano-Zs (Malvern Instruments, Worcestershire, UK and Zetasizer software 6.30, provided by the Center of Excellence for the Oceans, National Taiwan Ocean University) such that the particle diameters and the polydispersity index thereof of the SQ-liposomes are recorded.

The result of the aforesaid analysis shows that the particle diameters of phospholipid suspension particulates SQ-liposomes mainly fall within the range of 109.9±65 nm, with single peak distribution index PDI of 0.169, thereby verifying the following: squid's skin phospholipid is vibrated with an atomizer to produce the aerosol liposomes, and the distribution of the particle diameters of the aerosol liposomes recycled remains uniform, thereby ruling out rapid flocculation or fusion. The aerosol liposomes synthesized with the atomizer are in gas phase/aqueous phase/oil phase (G/A/O), gas phase/oil phase (G/O), or gas phase/oil phase/aqueous phase (G/O/A) and are presented in the form of suspended particulates.

According to the present invention, the method of producing a gaseous liposome comprises atomizing marine extract-derived phospholipid with an aerosol atomizer to synthesize the aerosol liposomes. To be specific, according to the present invention, the method of producing a gaseous liposome comprises: adding marine extract-derived solids, a marine extract-containing solvent, and a marine extract suspension to an aqueous solution to get diluted and atomized with an aerosol atomizer to synthesize the aerosol liposomes. Unlike the prior art, the present invention does not require separating functional phospholipids to undergo recombination with a view to forming liposomes. According to the present invention, the aerosol liposomes thus synthesized undergo cell membrane recombination before forming monolayer liposomes directly; hence, the PS groups of the marine extract are directly exposed from the liposome and thus recognized by macrophages.

Macrophage Engulf Aerosol Liposome of Squid Extract

Another study is conducted and associated with the present invention. The findings of the study are described below. In the study, squid's skin liposome is cultured with a culture medium to culture macrophage cell lines. The study shows that those macrophage cell lines which have engulfed liposomes accumulate plenty of vacuoles in cytoplasm. When their lipid droplets are stained with Nile red, fluorescence intensity increases with the concentration of squid's skin liposomes, indicating that macrophage cell lines did engulf squid's skin liposomes. Conventional intake routes of nutrients and drugs fall mostly within the following categories: topical, oral, intravenous, intraperitoneal, and subcutaneous. Since the gastrointestinal tract contributes to poor oral bioavailability of many drugs, the present invention resorts to the epithelium of the upper respiratory tract where phagocytosis is carried out by dendritic cells, monocytes, macrophages and so on which capable of shape variation, and in consequence inflammations are alleviated by efferocytosis.

According to the present invention, given a low culture medium height in the Petri dish placed in a semi-closed chamber, squid extract-derived aerosol liposomes are introduced to the lining of the upper respiratory tract to simulate the contact between each aerosol liposome and the pulmonary alveoli rife with macrophages for three hours. Observation under an inverted microscope reveals that plenty of vacuoles are accumulated in the cytoplasm of the macrophages, indicating that the macrophages did engulf aerosol liposomes.

Experiment on Macrophage cell line (RAW264.7) Engulfing Aerosol-Based Squid's Skin Liposome 10% FBS DMEM culture medium in a 6-well plate is inoculated with $2 \times 10^6$ RAW264.7 cells at 37° C. overnight. In the following, upon completion of cell attachment, the 10% FBS DMEM culture medium is replaced with 0.5 mL of serum-free culture medium, and the cells are divided into four groups. Each group undergoes the experiment twice repeatedly. Two of the four groups are covered with the plate cover to prevent the cells from coming into contact with the aerosol liposomes. Around hole of a diameter of 2 cm is formed on the plate cover which holds the other two groups. The cell culture plates are placed on an laminar flow and insulated with semi-transparent boxes. A round hole of a diameter of 6 cm is drilled with a driller in a lateral side of each box to connect with a ultrasonic atomizer pipe. The aerosol atomizer contains 7.5 mg/mL of squid's skin liposome (SQ-liposome) suspension. The atomized aerosol liposomes are delivered to the boxes through atomization holes thereof to simulate the upper respiratory tract and the aerosol liposomes adsorbed to the pulmonary alveoli. The aforesaid process lasts three hours before the cell culture plates are placed in an incubator at 37° C. in the presence of 5% $CO_2$ for three hours. Afterward, the culturing process is performed with a serum-free culture medium with a final concentration 1 μg/mL bacterial lipopolysaccharide (LPS) for 18 hours to collect a supernatant, so as to analyze various inflammation-related cytokines and inflammatory mediators.

Analysis of Cellular Survival Rate

After the supernatant has been collected, 0.5 mg/ml of MTT is added to the underlying cells to react for 30~60 minutes to remove the MTT from the supernatant. Then, tetrazolium bromide reacts with mitochondrial dehydrogenase (present in live cells only) to produce insoluble violet formazan. Afterward, cell membranes are cracked with DMSO to release violet crystals. Finally, the absorbance of A550 is assessed with an ELISA reader to analyze the cellular survival rate.

Prostaglandin E2

A commercially available prostaglandin E2 competitive enzyme immunoassay (EIA) kit (manufactured by Cayman, Ann Arbor, Mich., USA) or nitrate/nitrite colorimetric assay kit (manufactured by Cayman, Ann Arbor, Mich., USA) is used to assess PGE2 content in the supernatant. PGE2 (subject) in the supernatant culture medium competes with PGE2 (tracing agent) bonded by acetylcholinesterase and provided by the reagent for PGE2 monoclonal antibody. Afterward, the complex of PGE2 and monoclonal antibody is introduced into a microplate filled with goat anti-mouse polyclonal antibody and then cultured for an hour to remove any non-bound substances. Afterward, a substrate of acetylcholinesterase is introduced to react with Ellman's reagent so as to produce a yellow product whose absorbance is assessed at a wavelength of 412 nm. The higher the absorbance, the lesser is the PGE2 content of the sample. The PGE2 content of the sample is calculated with a standard curve obtained by performing serial dilution on standard samples.

Nitric Oxide Assay

Nitrite analysis reagent kids display colors usually by reacting Griess with deeply purple azo compounds. 80 μl of supernatant culture medium reacts with 10 μl of nitrate reductase and 10 μl of enzyme cofactors at room temperature for 1~3 hours before the introduction of 50 μl of Griess reagent 1 and Griess reagent 2 to increase the total volume to 200 μl, and undergo a reaction for 20 minutes in the dark to produce a violet product. Afterward, 540 nm absorbance is read by an ELISA reader, then compared with the standard curve of $NaNO_2$, and finally deducted a background value, to obtain the concentration of nitrite contained in the culture medium, thereby obtaining the NO yield indirectly.

Inflammation-related Cytokine Assay

A cytokine ELISA kit assesses inflammation-enhancing cytokines, including TNF-α, IL-1β and IL-6 and inflammation-inhibiting cytokines, including IL10 and TGF-β. The cytokines are assessed by a sandwich enzyme-linked immunosorbent assay, using reagents, including mouse TNF-α Enzyme-Linked Immune Substrate Assay (ELISA) kit (R &D system, USA), mouse IL-6 ELISA kit, mouse IL-1β ELISA kit, mouse TGF-β ELISA kit, and mouse IL-10 ELISA kit. The method of conducting the aforesaid experiment entails adsorbing diluted, captured antibodies to a 96-well plate, removing the antibodies on the following day, rinsing it with a rinsing buffer solution thrice, adding 300 μl of blocking reagent to fill completely any wells which the antibodies are not yet adsorbed to, allowing the reaction to take place for an hour, removing the blocking reagent, rinsing it with a rinsing buffer solution thrice, adding an appropriately diluted subject sample (cellular supernatant) to the 96-well plate, allowing the reaction to take place for two hours, removing the sample solution, rinsing it with a rinsing buffer solution thrice, reacting it with detection antibodies for two hours, removing any unadsorbed detection antibodies, introducing a substrate solution, i.e., tetramethylbenzidine substrate (NeA-Blue, Clinical science products Inc., USA) to display colors, terminating the color-displaying reaction with 2M sulfuric acid, detecting OD 450 nm absorbance with an ELISA reader, thereby obtaining the cytokine concentration of the subject sample by various cytokine standards and interpolation standard linear regression. The antibodies adsorbed to the TGF-β kit identify the antigen-determining region as linear; hence, before a sample assay is conducted to detect TGF-β contained in the sample solution, it is necessary to denature the target GF-β molecules under test with an acid then neutralize it with an alkali.

Statistical Analysis

All the data undergo statistical analysis with SAS 9.2 and one way analysis of variance (ANOVA), and is presented in the form of mean±standard error, so as to be compared by Duncan's multiple rang test (DMRT), where a significant difference and a very significant distance are indicated when $P<0.05$ and $P<0.01$, respectively.

Effect of Aerosol Liposome on aSQ-Liposome Mice Macrophage Cell Line (RAW264.7)-Associated Inflammation The experiment is conducted on four groups. Each group undergoes the experiment twice repeatedly. The four groups are a blank group (aSQ-liposome-, LPS-), squid's skin aerosol liposome processing control group (aSQ-liposome+, LPS-), bacterial lipopolysaccharide induction group (aSQ-liposome-, LPS+) and squid's skin aerosol liposome processing+bacterial lipopolysaccharide induction experimental group (aSQ-liposome+, LPS+). The results of the experiment are shown in Table 2 below.

TABLE 2

Effects of aerosol liposomes on LPS-induced Raw264.7

| group | cellular survival rate (%) | prostaglandin E2 (μg/ml) | nitric oxide (μM) | tumor necrosis factor (μg/ml) |
|---|---|---|---|---|
| aSQ-iposome−, LPS− | 100 | 0.12 ± 0.0 | 0.87 ± 0.03 | 1.59 ± 0.02 |
| aSQ-iposome+, LPS− | 85.5 ± 2.6 | 0.22 ± 0.0 | 1.2 ± 0.02 | 7.85 ± 0.02 |
| aSQ-iposome−, LPS+ | 89.9 ± 2.1* | 2.7 ± 0.1* | 27.18 ± 0.34* | 37.72 ± 0.46* |
| aSQ-iposome+, LPS+ | 89.5 ± 2.8# | 1.07 ± 0.1# | 4.86 ± 0.23# | 14.36 ± 0.46# |

| group | interleukin-1β (μg/ml) | interleukin-6 (μg/ml) | interleukin-10 (pg/ml) |
|---|---|---|---|
| aSQ-iposome−, LPS− | 0.22 ± 0.0 | 0.118 ± 0.0 | 13.3 ± 0.2 |
| aSQ-iposome+, LPS− | 0.24 ± 0.0 | 0.09 ± 0.0 | 15.6 ± 0.2 |
| aSQ-iposome−, LPS+ | 1.62 ± 0.3* | 24.39 ± 0.2* | 105.9 ± 01.6* |
| aSQ-iposome+, LPS+ | 0.4 ± 0.0# | 7.5 ± 0.1# | 293 ± 1.8# |

Note:
aSQ-liposome, squid's skin aerosol-based liposome processing;
*very significant difference (P < 0.01), when compared with blank group (aSQ-iposome−, LPS−);
very significant difference (P < 0.01), when compared with bacterial lipopolysaccharide induction group (aSQ-liposome−, LPS+).

After an inflammation induced by Raw264.7 cell with 1 μg/ml of LPS has lasted 18 hours, it is observed that the concentrations of nitric oxide, prostaglandin E2, and inflammatory mediators secreted by Raw264.7 cells in the cellular supernatant increase from 0.12 μg/ml to 2.7 μg/ml and from 0.87 μM to 27.2 μM, respectively, indicating the Raw264.7 cells are induced to trigger an inflammation process. If squid's skin aerosol liposomes are pre-treated for three hours, concentrations of prostaglandin E2 and nitric oxide in the cellular supernatant decrease significantly to 1.07 μg/ml and 4.86 μM (P<0.01), respectively, indicating that the performance of the inflammatory mediators reduces if the aerosol liposomes are pre-treated.

The aforesaid phenomenon also occurs to the reduction in the performance of inflammation-enhancing cytokines, also known as pro-inflammatory cytokines, wherein the concentrations of tumor necrosis factor (TNF-α), interleukin-1β (IL-1β) and interleukin-6(IL-6) increase from 1.59, 0.22 and 0.11 μg/ml to 37.72, 1.62 and 24.39 μg//ml, respectively, after an inflammation induced by Raw264.7 cells with bacterial lipopolysaccharide (LPS) has lasted 18 hours. If the aerosol liposomes are pre-treated, the aforesaid concentrations decrease to 14.36, 0.4 and 7.5 μg/ml, respectively, indicating a very significant reduction in the concentration (P<0.01) of inflammation-enhancing cytokines associated with the inflammation induced with LPS.

The opposite phenomenon occurs to the regulation of interleukin-10. Interleukin-10 is generally believed to be capable of alleviating inflammations. After an inflammation has been induced by Raw264.7 cells with LPS treated, the concentration of interleukin-10 in the supernatant increases from 13.3 pg/ml to 105.9 μg/ml. By contrast, the concentration of interleukin-10 in the aerosol liposomes pre-treating group increases greatly to 300 μg/ml, that is, threefold that of the LPS group, indicating that the pre-treating of the aerosol liposome not only decreases the performance of pro-inflammation cytokines, but also increases the secretion of anti-inflammation cytokines (P<0.01).

Both the survival rate of Raw264.7 cells which engulf aerosol liposomes and the survival rate of Raw264.7 clls which undergo LPS induction are higher than 85%. This proves the following: low toxicity of aerosol liposomes on Raw264.7 cells; and the performance of inflammatory mediators, Pro-inflammation cytokines, and anti-inflammation cytokines are not affected by the cytotoxicity of the aerosol liposomes on Raw264.7 cells.

The aqueous phase of the outermost layer of the aerosol liposomes further comprises nucleic acid matter, cytokines, or ions. In a physiological environment, the nucleic acid matter, cytokines, or ions induce the chemotaxis of the macrophages. Regarding the method of producing an aerosol liposome according to the present invention, the nucleic acid matter, cytokines, or − ions are added to the aqueous solution.

The aforesaid experimental results show that an aerosol liposome of a marine extract, as provided by the present invention, is simple and stable and can be absorbed through the mouth, nose, upper respiratory tract, and epidermis and engulfed by macrophages therein to quickly alleviate or regulate systematic inflammatory responses and prevent inflammation-related diseases.

The present invention is disclosed above by preferred embodiments. However, persons skilled in the art should understand that the preferred embodiments are illustrative of the present invention only, but should not be interpreted as restrictive of the scope of the present invention. Hence, all equivalent variations and replacements made to the aforesaid embodiments should fall within the scope of the present invention. Accordingly, the legal protection for the present invention should be defined by the appended claims.

What is claimed is:

1. An aerosol liposome of a marine extract, the marine extract being extracted from cell membranes of marine processing streams, comprising phosphatidylserine (PS), phosphatidylcholine (PC), phosphatidylethanolamine (PE), phosphatidylinositol (PI), and lysophosphatidylcholine (LysoPC), including at least phosphatidylserine (PS), characterized in that:
   the aerosol liposome is of a particle diameter of less than 10,000 nm, and a surface of the aerosol liposome carries phosphatidylserine (PS) molecules;
   wherein the marine extract is from squid's skin, mackerel's head, milkfish's visceras, tilapia's visceras, red seabream's visceras, and bonitos' visceras.

2. The aerosol liposome of claim 1, wherein the aerosol liposomes are in gas phase/aqueous phase/oil phase (G/A/O), gas phase/oil phase (G/O), or gas phase/oil phase/aqueous phase (G/O/A).

3. The aerosol liposome of claim 1, wherein the aerosol liposomes each have a particle diameter of 20~10,000 nm.

4. The aerosol liposome of claim 1, wherein the aerosol liposomes each have a particle diameter of 50~300 nm.

5. The aerosol liposome of claim 1, wherein the aerosol liposomes are essentially monolayer particulates.

6. The aerosol liposome of claim 1, wherein an aqueous phase of an outermost layer of the aerosol liposome further comprises a member selected from the group consisting of nucleic acid matter, cytokine, and valent ion.

7. A method of producing an aerosol liposome, for producing the marine extract aerosol liposome of claim 1, comprising the step of atomizing the marine extract into the aerosol liposome with an aerosol atomizer.

8. The method of claim 7, wherein marine extract-derived solids, a marine extract-containing solvent, and a marine extract suspension are added to an aqueous solution to get diluted and atomized with an aerosol atomizer to synthesize the aerosol liposomes.

9. The method of claim 8, wherein a member selected from the group consisting of the nucleic acid matter, cytokine, and ion of claim 7 is added to an aqueous solution.

* * * * *